(12) United States Patent
Code

(10) Patent No.: US 8,021,610 B2
(45) Date of Patent: *Sep. 20, 2011

(54) SYSTEMS PROVIDING ANTIMICROBIAL ACTIVITY TO AN ENVIRONMENT

(75) Inventor: Kenneth R. Code, Edmonton (CA)

(73) Assignee: BioLargo Life Technologies, Inc., Irvine, CA (US)

( * ) Notice: Subject to any disclaimer, the term of this patent is extended or adjusted under 35 U.S.C. 154(b) by 686 days.

This patent is subject to a terminal disclaimer.

(21) Appl. No.: 11/973,933

(22) Filed: Oct. 11, 2007

(65) Prior Publication Data

US 2008/0095812 A1    Apr. 24, 2008

Related U.S. Application Data

(63) Continuation-in-part of application No. 11/516,960, filed on Sep. 7, 2006, now Pat. No. 7,867,510.

(51) Int. Cl.
*A61L 2/20* (2006.01)
(52) U.S. Cl. .............................. 422/37; 422/28; 424/670
(58) Field of Classification Search .................... 422/28, 422/37; 424/670
See application file for complete search history.

(56) References Cited

U.S. PATENT DOCUMENTS

| | | | |
|---|---|---|---|
| 3,708,263 A | 1/1973 | Boucher | 422/20 |
| 4,375,535 A | 3/1983 | Kightlinger et al. | 527/313 |
| 4,497,930 A | 2/1985 | Yamasaki et al. | 524/556 |
| 4,731,391 A | 3/1988 | Garvey | 521/137 |
| 4,888,118 A | 12/1989 | Barnes et al. | 210/668 |
| 5,019,495 A | 5/1991 | Shanbrom | 435/1.1 |
| 5,128,149 A | 7/1992 | Shanbrom | 424/529 |
| 5,128,150 A | 7/1992 | Shanbrom | 424/533 |
| 5,176,836 A | 1/1993 | Sauer et al. | 210/670 |
| 5,186,945 A | 2/1993 | Shanbrom | 424/529 |
| 5,227,161 A | 7/1993 | Kessler | 424/94.4 |
| 5,265,302 A | 11/1993 | Sivacoe | 15/104.061 |
| 5,324,438 A | 6/1994 | McPhee et al. | 210/748 |
| 5,360,605 A | 11/1994 | Shanbrom | 424/78.08 |
| 5,370,869 A | 12/1994 | Shanbrom | 424/78.22 |
| 5,384,929 A | 1/1995 | Smith | 15/104.061 |
| 5,419,902 A | 5/1995 | Kessler | 424/94.4 |
| 5,482,720 A * | 1/1996 | Murphy et al. | 424/489 |

(Continued)

FOREIGN PATENT DOCUMENTS

DE    2029 598    6/1970

(Continued)

OTHER PUBLICATIONS

PCT International Search Report and The Written Opinion of the Internatoinal Searching Authority dated Sep. 18, 2009, from related patent application PCT/US2009/04248.

(Continued)

*Primary Examiner* — Walter D Griffin
*Assistant Examiner* — Timothy Cleveland
(74) *Attorney, Agent, or Firm* — Mark A. Litman & Associates, PA

(57) ABSTRACT

A process reduces the microbial content in land mass by providing molecular iodine in the land mass in a concentration in aqueous material in the land mass of at least 5 or 10 parts per million. The molecular iodine may be added in gaseous or liquid or solid state, and may be formed in situ using available water, added water and/or alcohol in the reaction.

22 Claims, 1 Drawing Sheet

U.S. PATENT DOCUMENTS

| | | | | |
|---|---|---|---|---|
| 5,496,527 | A * | 3/1996 | Yokogawa et al. | 423/338 |
| 5,589,072 | A | 12/1996 | Shanbrom | 210/638 |
| 5,609,864 | A | 3/1997 | Shanbrom | 424/78.08 |
| 5,629,024 | A | 5/1997 | Kessler et al. | 424/667 |
| 5,635,063 | A | 6/1997 | Rajan et al. | 210/266 |
| 5,639,481 | A | 6/1997 | Kessler et al. | 424/667 |
| 5,648,075 | A | 7/1997 | Kessler et al. | 424/94.4 |
| 5,695,458 | A | 12/1997 | Shikani et al. | |
| 5,772,971 | A | 6/1998 | Murphy et al. | 422/292 |
| 5,849,291 | A | 12/1998 | Kessler | 424/94.4 |
| 5,885,592 | A | 3/1999 | Duan et al. | 424/400 |
| 5,903,946 | A | 5/1999 | Collins et al. | 15/104.061 |
| 5,924,158 | A | 7/1999 | Watts | 15/104.061 |
| 5,948,385 | A | 9/1999 | Chapman et al. | 424/1.29 |
| 5,962,029 | A | 10/1999 | Duan et al. | 424/613 |
| 6,037,019 | A | 3/2000 | Kooyer et al. | 427/598 |
| 6,067,682 | A | 5/2000 | Rankin | 15/104.061 |
| 6,071,415 | A | 6/2000 | Frommer et al. | 210/669 |
| 6,139,731 | A | 10/2000 | Harvey et al. | 210/175 |
| 6,146,725 | A * | 11/2000 | Code | 428/35.2 |
| 6,248,335 | B1 | 6/2001 | Duan et al. | 424/400 |
| 6,261,577 | B1 | 7/2001 | Kessler | 424/401 |
| 6,328,929 | B1 | 12/2001 | Code | 422/29 |
| 6,403,674 | B1 | 6/2002 | Schubert | 522/167 |
| 6,432,426 | B2 | 8/2002 | Kessler | 424/401 |
| 7,000,280 | B1 | 2/2006 | Knapp | 15/104.061 |
| 7,033,509 | B2 | 4/2006 | Klein et al. | 210/753 |
| 7,192,911 | B2 | 3/2007 | Sunder et al. | 510/223 |
| 7,431,849 | B1 * | 10/2008 | Swearingen et al. | 210/749 |
| 2001/0019728 | A1 * | 9/2001 | Basinger et al. | 424/667 |
| 2002/0174674 | A1 * | 11/2002 | Takahashi et al. | 62/264 |
| 2003/0135172 | A1 | 7/2003 | Whitmore et al. | |
| 2003/0185704 | A1 * | 10/2003 | Bernard et al. | 422/37 |
| 2004/0167048 | A1 | 8/2004 | Sunder et al. | 510/220 |
| 2004/0267223 | A1 | 12/2004 | Etchells | 604/385.01 |
| 2005/0196593 | A1 | 9/2005 | Campbell et al. | |
| 2008/0095812 | A1 | 4/2008 | Code | |

FOREIGN PATENT DOCUMENTS

| | | |
|---|---|---|
| EP | 439 878 | 8/1991 |
| EP | 446 761 | 9/1991 |
| EP | 611 206 | 8/1994 |
| GB | 2344997 | 6/2000 |
| WO | WO93/21299 | 10/1993 |
| WO | WO98/24486 | 6/1998 |
| WO | WO01/28598 | 4/2001 |
| WO | WO 02058748 A1 * | 8/2002 |

OTHER PUBLICATIONS

S.S. Block; "Sterilization, Disinfection and Preservation" 2001, Lippincott, PA XP002544842 pp. 159-183.

Supplementary Partial European Search Report from related EP patent application EP 07 75 4079 dated Sep. 9, 2009.

M. Abdalla, et al., *Ioddimetric Determination of Iodate, Bromate, Hypochlorite, Ascorbic Acid and Thiourea Using Flow Injection Amperometry*. Dept of Chem, College of Sci, King Saad Univ, Saudi Arabia Analyst, May 1989, vol. 114, p. 583-586, especially p. 583.

Foret, et al., *The Effect of Free Iodine on the Germicidal Activity of Iodine Teat Dips*. Milkproduction.com, Dec. 12, 2002., Especially Tables 103.

P. Kapur and M. Verma, "Determination of Iodate Ion in Presence of Cupric Ion", Industrial and Engineering Chemistry Analytical Ed.; vol. 13, No. 5 (May 1941). p. 338.

Science Direct—Microbiological Research: Detection of antimicrobial activities and bacteria, "Detection of Antimicrobial activities and bacteriocin structural genes in faecal *Enterococci* of wild animals." www.sciencedirect.com Feb. 18, 2011 (2 pgs).

Sally N. Jewell, et al., "Rapid detection of lytic antimicrobial activity against yeast and filamentous fungi," Journal of Microbiological Methods 49 (2002) pp. 1-9.

J. Durodie, et al., "Repid Detection of Antimicrobial Activity Using Flow Cytometry," Cytometry 21:374-377 (1995).

www.freerpatentsonline.com/4311794.html, "Determination of bacterial growth activity and antibiotic sensitivity by catalase measurement," U.S. Appl. No. 06/160,682 (19 pgs).

Aac.asm.org/cgi/content/full/45/12/3456, "Measurement of Effects of Antibiotics in Bioluminescent *Staphylococcus aurea* RN 4220," Mervie Tenhami, et al. (3 pgs).

"Screening and Identification Methods for official control of Banned Antibiotics and Growth promoters in Feedingstuffs," Jose Nunes da Costa, et al. May 4, 2004 (10 pgs).

* cited by examiner

SYSTEMS PROVIDING ANTIMICROBIAL ACTIVITY TO AN ENVIRONMENT

RELATED APPLICATION DATA

The present Application claims priority as a continuation-in-part of U.S. patent application Ser. No. 11/516,960, filed Sep. 7, 2006 now U.S. Pat. No. 7,867,510.

BACKGROUND OF THE INVENTION

1. Field of the Invention

The present technology relates to the field of antimicrobial protection, particularly antimicrobial activity in close proximity to environments that need to be protected from or cleansed of microbial or chemical material that might be of concern. These include closed and open environments, and environments adjacent patients or users. The present technology also describes systems for delivery of the antimicrobial activity. The present technology relates to the field of antimicrobial protection, particularly antimicrobial activity in close proximity to hard surfaces, enclosed environments, rooms, and the bodies of patients. In particular, the field relates to the use of antimicrobial, antiodor and chemical modification agents that are active in the presence of water and/or lower molecular weight alcohols (e.g., C1-C6 alcohols).

2. Background of the Art

Historically, soils contaminated by solvents, oils, waste spillage and similar organic materials through leakage from storage or piping, accidental spills or inadequate disposal have been managed in several ways. Representative of the approaches which have been taken are: (1) excavation and reburial in an approved landfill; (2) soil flushing using recovery and recharge wells; and (3) in-situ biological treatment using supplemental nutrients and possibly supplemental bacteria. Other forms of localized antimicrobial activity use heat, disinfectants, aerosols and the like, but have limited applications, and highly diverse systems are created for different environments to be treated.

These land treatment methods particularly have not been entirely satisfactory for a host of technical, legal and cost reasons. Excavation and reburial of even moderate size tracts of contaminated soil is enormously costly. Moreover, even properly designed and operated state-of-the-art landfills have been found to leak. Soil flushing has serious technical limitations in that very large volumes of water must be flushed through the soil to sufficiently lower contaminant concentrations. In-situ biological treatment also possesses drawbacks, among them its unsuitability in areas with low groundwater and its high cost and the need to introduce new bacteria into an ecological region.

An alternative method of treatment for soils containing easily volatilized contaminants was attempted by the U.S. Environmental Protection Agency ("EPA") in 1984. The contaminated soil, containing 1,1,1 trichloroethane, trichloroethene, toluene, ethyl benzene and ortho-, meta-, and para-xylene in concentrations from 10,000 to 110,000 ppb., was fed through an asphalt drying unit, also known in the industry as an aggregate dryer or rotary kiln. The drying unit included a liquid propane burner at one end which supplied combustion gases at 375° F. to the interior of the dryer. From exposure to the 375° F. gas, the contaminants were vaporized and the combined mixture of gases passed through a cyclone and bag house for removing particulate emissions, and then discharged directly to the atmosphere. The treated soil was discharged from the dryer, collected and then returned to the site.

Although the foregoing method was reported to be effective in reducing the concentrations of some contaminants by at least 99%, serious drawbacks were evident. Volatile organic compounds ("VOC's") removed from the soil being treated were discharged to the atmosphere, thus decontaminating one medium, the soil, at the expense of polluting another medium, the air. In order to dilute the concentration of emitted VOC's in the ambient air, and because of local air discharge requirements, the dryer could only be operated at a feed rate of 10-15 tons of soil per hour, rather than the design rate of 100 tons/hour. Localities with more stringent air quality regulations would necessitate an even lower feed rate. Furthermore, the dryer could only be operated in dry weather conditions to prevent the emitted VOC's from being scrubbed from the atmosphere by rainfall, and thus returned to the soil.

For a proper site remediation project, both contaminated soil and contaminated groundwater must be cleaned. The contamination becomes very serious if the groundwater is a drinking water source. About 70 percent of potable water in the U.S.A. is supplied by groundwater. Site contamination, which is a national major concern, is about 71 percent caused by industrial accidents (chemical spills, tank leaks, etc.), 16 percent caused by railroad or truck's chemical accidents, and 13 percent caused by leachates from lagoons or dumpsites.

The primary reason for cleaning soil is public health protection. The primary reasons for treating groundwater are: potable use (39 percent), clean-up of aquifer to prevent spread of contamination (48 percent), and industrial and commercial use (13 percent). In any case, the potentially hazardous VOCs must be removed. Timely clean-up of aquifer to prevent spread of contamination is extremely important because the damage can be beyond repair if the spread of contamination is too wide.

The present technologies for ground and groundwater treatment include: air stripping tower without air emission control, non-regenerative gas phase granular activated carbon, chemical oxidation, non-regenerative liquid phase granular activated carbon, active charcoal fiber, biological processes, ion exchange, ultrafiltration, $H_2O_2$ treatment, reverse osmosis (RO), ozonation, lime softening, ultraviolet (UV), chemical coagulation, sedimentation, filtration and halogenation (e.g., chlorination, bromination and iodization). Air stripping tower without air emission control is the most common process for VOCs removal, but is not acceptable in many states. Liquid-phase granular activated carbon (GAC) contactor is technically feasible for water purification, but may be economically unfeasible when it is used alone. Chemical oxidation alone or UV alone is not cost-effective for VOCs reduction. Certain chemicals may even give undesirable residuals. Ultrafiltration and RO are excellent post-treatment process, requiring adequate pretreatment for cost reduction. Biological process is very efficient for removal of organic contaminants, but causes air pollution and requires thorough disinfection.

While conventional ozonation, UV, RO and chlorination are all effective disinfection processes, they all require separate reactors.

The story is quite different for soil treatment are quite limited and more narrowly focused because of the complexities in working with masses and volumes of solids. The present technologies for soil cleaning include: surfactant washing, neutralization, solidification, incineration, chemical oxidation, bio-oxidation, lime treatment, venting, and the like.

U.S. Pat. No. 7,033,509 (Klein) discloses an iodine fluid purification process using a source of fluid and means for delivery of iodine to the source of fluid for use in the purification process. The process provides a means for recovery of the iodine and/or iodine and/or other iodine species derived from the iodine, from the fluid.

U.S. Pat. No. 5,176,836 discloses a water purification process or method by introduction of molecular iodine into the water supply to impart a desired iodine residual wherein the water is passed through an iodinated anion exchange bed wherein the concentration of $I_2$ in the flowing water gradually decreases and the ion bed is recharged by treatment with an aqueous iodine solution produced by flowing water through a bed of iodine crystals having connections in parallel with the ion exchange bed and activated periodically e.g., by a timer, by measured flow of water or by residual level to recharge the bed. That system provides for long term microbiological control in water suitable for potable activities.

The majority of patents relates to the direct or indirect treatment of water to remove microbes. Such disclosures are shown in U.S. Pat. No. 6,863,905; the use of free elemental iodine to kill or inactivate a large range of microbes (bacteria, virus and other pathogens) particularly in protein-containing solutions such as human blood, human plasma or fractions thereof is described in U.S. Pat. Nos. 5,019,495; 5,128,149; 5,128,150; 5,186,945; 5,360,605; 5,370,869; 5,589,072; and 5,609,864; pentavalent iodine-impregnated resins U.S. Pat. No. 5,635,063; provision of potable water U.S. Pat. Nos. 6,139,731 and 6,071,415; 5,324,438 describes a process for oxidizing a compound comprises contacting the compound with iodide ions and irradiating the iodide ions with UV light of a wavelength sufficient to generate iodine atoms. The compound is then oxidized with the resulting iodine atoms. The iodine atoms are reduced to iodide ions as a result of the oxidation of the compound.

Pesticides can influence soil microbial activity, at times paradoxically. Application of paraquat led to buildup of fungi and bacteria, but reductions in $CO_2$ production, cellulose degradation, and nitrogenase activity. Sometimes selective destruction of predators and the resultant buildup of their microbial prey can occur. For example, glyphosate or diquat+paraquat application led to the buildup of *Gaeumannomyces graminis* var. *tritici*, the causal agent of take-all disease of wheat. Inoculation with untreated soil led to suppression of the pathogen in the treated soil, suggesting the possible role of microbial antagonists.

Nitrification and symbiotic nitrogen fixation are especially sensitive to disruption by pesticides, probably in part due to the small numbers of species involved in these processes.

There are many instances where aqueous materials are retained in contact with animal bodies and in which there is potential for unwanted and even dangerous and significant microbial growth or microbial introduction into the animal body. For example, in the application of materials wound dressing, menstrual products, patches, diapers, pads and the like, moisture from the animal body or ambient conditions or the materials themselves can introduce microbes to the environment and those microbes can proliferate in the vicinity of the materials when moisture is present. The uncontrolled growth of random microbes is seldom beneficial and has been the subject of significant efforts at control.

U.S. Pat. Nos. 6,328,929 and 6,146,725 (Code) describe reagent and delivery compositions for formation of iodine gas or iodine in water.

Many applications exist where it is still necessary or at the very least an advantage for improves systems and agents to be present which demonstrate anti-bacterial, anti-mycotic activity or both, resulting in the control of bacterial and/or fungal growth. For example, an apparatus or article as a whole or in part may have the property of suppressing bacterial and fungal growth. Control of bacterial and/or fungal growth may be through the prevention or inhibition of the growth of such microbes.

SUMMARY OF THE INVENTION

Systems and materials are provided to environments, enclosed areas, soil systems, water systems, and patients to be treated which generate an iodine gas-rich or iodine-dissolved-in-water rich environments that can provide antimicrobial activity or antichemical activity in a controlled environment or location. The iodine environment can be provided in numerous formats and in varied tasks and services. It is particularly desirable to provide the reactive ingredients in a format in which at least one of the chemical components and preferably each of the chemical components (reagents) or both of the chemical components are encapsulated, coated, or otherwise provided in a form with an immediate (close physical proximity such as a coating or packet), yet water-removable, barrier to ambient moisture and incidental water.

The present technology also includes an article for application, association with or attachment to an environment that is to be treated with an iodine-rich environment, including closed environments such as vehicle cabs, vehicle seating areas, rooms, crates, containers, dishwashers, refrigerators, freezers, enclosed gas and liquid circulation systems (e.g., air conditioning pipes and conduits, heating pipes and conduits, and open environments such as fields, lawns, parks, orchards, farm fields, greenhouses, and adjacent the bodies of animals (including humans) to provide both absorbency and antimicrobial activity. The article and treatments may be any delivery system that can deliver the iodine-rich environment as needed to an appropriate target. The delivery may be as a gas ($I_2$ or iodine containing), packets (with reactants), tablets (with reactants), films, powders, packets, pouches, multiple chamber packets, concentrates, liquids and the like that may be carried in fibrous supports, film supports, free-flowing, breakable, pourable or otherwise deliverable forms such as bottles, capsules, packets, diaper, gauze, padding, sanitary sheets or the like and may comprise a water absorbent material; and a composition that reacts with water to produce molecular iodine. The composition is delivered to provides a local concentration of at least 5 parts and preferably 10 parts per million iodine in water carried by the material when the material has 5% by weight of water present in the water absorbent with respect to the total weight of the water absorbent material or concentrations that are sufficiently concentrated in air to address antimicrobial requirements or provide sufficient chemical activity to mediate the concentration of the targeted chemical in the environment. The 5 parts provides stabilizing to partial reduction of chemistry and microbes, while the at least 10% provides strong to complete antimicrobial activity, with intermediate effects when at least 6%, at least 7%, at least 8%, and at least 9% parts by weight iodine in the water. The composition provides a local concentration of at least 5 and preferably 10 parts per million iodine in alcohol and/or water carried to the surface or carried by the material. To fully activate the material there may be as little as 5% by weight solids in the activating water and/or alcohol (C1-C6 aliphatic, branched or cyclic alcohol) present respect to the total weight of the water absorbent material.

DETAILED DESCRIPTION OF THE INVENTION

Figure 1:
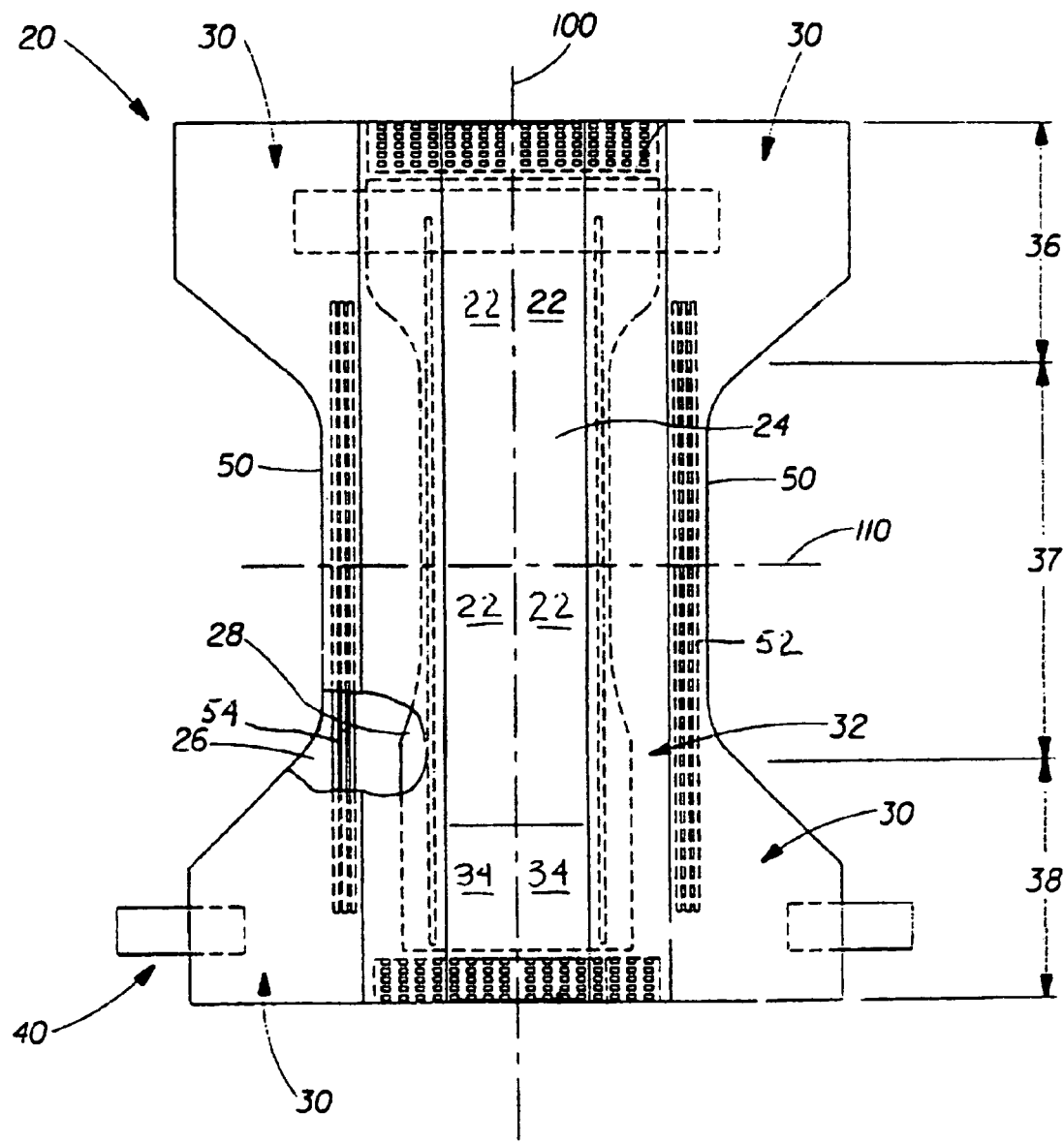
FIG. 1 shows an inside view of an opened diaper product.

The composition of the present technology is activatable by contact with water, alcohol and/or alcohol/water compositions. The alcohols of primary consideration are the aliphatic and branched lower molecular weight alkanols such as methanol, ethanol, propanol, iso-propanol, butanol, t-butanol, i-butanol, pentanol, hexanol and the like in the one to six carbon atom length alcohol group. The compositions have any of an antimicrobial activity, anti-odor activity, and the like and may oxidize harmful and/or toxic chemicals by release of the composition's active ingredients.

The potential for health risks by the presence of bacteria has been repeatedly noted in the literature. As recently as 2006, a soil-borne bacterial infection called melioidosis has killed 24 people in Singapore, making it more deadly than SARS or bird flu. This illness, also known as Whitmore's Disease, is listed by the U.S. government as a potential biological weapon but Singapore government officials said there was no sign it had been spread intentionally. The bacteria enter the body when bruised skin comes into direct contact with contaminated soil or water, leading to abscesses and blood poisoning. Victims experience fever, coughing and shortness of breath. In some cases they develop pneumonia. The death rate hit 40 percent between January and July this year, up from 10 percent in recent years. Up to early September 2005, 79 people were diagnosed with the disease. That death rate was three times that of Severe Acute Respiratory Syndrome (SARS), which killed 13 percent of sufferers.

Additionally, it has become apparent that the overuse of antibiotics in agricultural environments has accelerated the frequency of appearance and rate of appearance of antibiotic resistant bacterial strains in soils. This complicates the means of treating bacteria in soil and makes the total removal of bacterial contaminants from soil imperative so that the resistant strains do not move into the general animal population and the human population Other bacteria may be introduced to the soil in accidental spills. Confined areas, which are herein defined as volumes that do not replace at least 50% (preferably does not replace at least 25% or at least 10% or most preferably less than 10% or less than 5%) of the volume of gas (vapor) or liquid (water or aqueous materials) volume within 2 minutes (e.g., a container, shed, room, trailer, tanker, silo, restroom, office, automobile, truck cab, plane cabin, dishwasher, oven, refrigerator, freezer, cooler, operating room, sterilization box, building, and the like) can be treated by processes according to the present technology. For example, the technology includes a process for reducing the microbial content in a confined area by providing at least two reagents that react in the presence of water to form $I_2$ into the confined area and providing water to provide a concentration in aqueous material in vapor or liquid within the confined area of at least 5 or at least 10 parts per million $I_2$ in air or $I_2$/water. As noted elsewhere herein, the reactants are preferably transported and introduced into the environment as solids with at least one of the reagents coated to prevent premature reaction from especially atmospheric moisture. Single coatings (e.g., a polymer, a sugar, starch or inorganic material, such as silica particle shell) or multiple coatings (a polymer layer and silica particle shell) may be used as the coating. Greater numbers of layers or coatings are possible, but the lower numbers simplify manufacture and use.

One way of providing molecular iodine ($I_2$) on site (to the confined area, device, container, water, soil, etc.) with a delivery system or directly onto a ground environment (especially rather than having to transport all of the soil or water to a treatment site, or bring all equipment and conduits top a treatment facility) is to provide reactants that can readily produce molecular iodine on-site in a controllable reaction. One format of providing the molecular iodine would be through the oxidation-reduction reaction between two salts or compounds or a metathesis reaction to produce the molecular iodine. It is a readily controlled environment where the reaction can be performed in an aqueous environment. One reaction that can effect this would be generically described as:

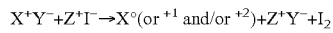

In this reaction scheme, X is a metal (preferably a multivalent metal and more particularly a divalent metal), Y is an anion (preferably a multivalent anion and more preferably a divalent anion, and an anion having at least two oxygen atoms), Z is an alkali metal or alkaline cation. Examples of X are copper, iron, manganese, lead, nickel, tin, and the like, Y can be sulfate, sulfite, sulfonate, carbonate, phosphate, phosphate, nitrate, nitrite, borate, and the like, and Z can be sodium, lithium, potassium, ammonium, magnesium, aluminum, and the like. One preferred reaction would be:

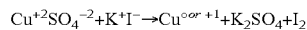

This reaction takes place readily in an aqueous environment and produces molecular iodine at a controlled rate. The reaction may be used by wetting, dispersing or dissolving the molecular iodide and allowing the iodine in the carrying material to be released and carried to the site (which may be the carrying material itself, such as the fabric, clay, fibers, film etc.) and to penetrate the area intended to be treated. The iodine may persist for sufficient time to treat the area, particularly within a wetted material on the surface of a patient. The reaction may also be used by dispersing or mixing the two ingredients into the carrying material (e.g., the fabric, fiber, film, sheet, etc.), either with additional water provided, with water of hydration on the first reactant (e.g., $X^+Y^-.nH_2O$, such as $CuSO_4.5H_2O$) or with ambient water in the carrying material. The two reactants may be physically separated from each other before being combined for application or reaction, as in separate capsules, fibers, layers or the like. The two reactants may be provided as a solid carrier medium that separates the two reactants until they are in contact with water (as in a soluble carrier such as polyvinyl alcohol, gelatin, amylase, starch, sugars such as mannitol or rabbitol, which tend to be more substantive that sucrose and fructose and the like, in pellet, fiber, dust, particle or block form). The two reactants may be independently coated with a soluble/dispersible coating and the two ingredients kept in a single water-penetrable layer, and the layer itself may be further protected from moisture as in a sealed envelope or package.

In using the technology described herein in an enclosed environment, not only may the environment itself bet treated (the office, the dishwasher, the restroom, etc.), but also individual or collections of items in the enclosed area or environment can be and are treated. Surgical instruments may be placed within a sterilization box, dishes may be in the dishwasher, luggage or boxes within a storage area, and the like may also be individually or collectively treated by the technology because of the high penetrating capability of the iodine gas or iodine dissolved in water.

It has been recently noted that the use of lower water temperatures in both clothes washing machines and dishwashing machines has allowed the proliferation of transmitted infections because of reduced sterilization. The use of soaps alone is not sufficiently antimicrobial to offset the reduced temperatures in these washing conditions. Appropriate amounts of delivered $I_2$ according to the present invention will be sufficient to at least return antimicrobial activity in these washing environments to traditionally safe or safer levels.

Although the materials of the described technology may be provided in a vast array of materials and compositions applied to the surface of patients, such as bandages, BandAids® strips, diapers, gauze, wraps, sanitary napkins, tampons, plugs, sheet coverings (e.g., on beds) and the like, the discussion will emphasize diapers and incontinence diapers for simplifying the disclosure, without intending to limit the scope of the invention. The reagents and especially the moisture-protected reagents can be added to other materials for inclusion into various delivery formats. For example, previously formed protected reagents (as a single particle with two ingredients, multiple particles with individual reagents, or mixtures of the two types of particles) may be blended with a carrier, preferably a carrier that tends to support the particles and prevent them from falling out of the carrier. This can be done by spray applying the reagent particles onto a carrier (e.g., fabric, filaments, fibers, film) with sufficient tackiness or adherent capability between the particles and the carrier to retain the particles during use. For example, the fabric or fibers may be tacky, a contemporaneously applied tacky material (e.g., adhesive) may be sprayed with application of the particles, and the like. As the particles are initially formed (usually with a drying step involved), the partially dried (and probably tacky) particles may be sprayed, blended or mixed with fibers, filaments or other carriers and the drying surface of the particles will cause the particles to adhere to other surfaces with sufficient strength that a carrier system is provided.

The technology described herein may also be performed by applying a solid carrier system to a patient or a confined area, and awaiting the presence of sufficient water on or in the carrier system to activate the ingredients and cause the gaseous iodine to form in sufficient concentration in the solid carrier to attenuate, reduce or eliminate bacterial growth in the solid carrier or the confined area. A simple format, in considering diaper-like materials for any age animal, would include at least the following formats:

1) particulate and separate reactants may be carried in the same layer of the diaper;
2) particulate and separate reactants may be carried in different layers of the diaper;
3) particulate reactants may be carried in the same pellets in an anhydrous condition in the same layer of a diaper;
4) the particulate reactants may be adhered to the same or separate fibers or films that are associated with on constitute the diaper;
5) the reactants may be carried in fiber materials dispersed throughout or partially constituting the structure of the diaper;
6) capsules or microcapsules of the reactants in water-soluble or water-dispersible shells may be distributed throughout the diaper; and
7) a film or films (water-soluble, water-dispersible or water-leachable) may carry one or more of the reactants, with the other reactant in a location that released or carried first reactant will be placed into contact with the second reactant in the presence of water.

Other formats and process may be used as long as the presence of water on the carrier system enables the generation of gaseous molecular iodine within the carrier in sufficient concentration to act as a microbicide.

The process may use the above reaction to form the molecular iodine represented by $$XY + ZI \rightarrow X° + ZY + I_2$$

wherein X is a metal, Y is an anion, Z is an alkali metal or alkaline cation, or where X is a multivalent metal, Y is a multivalent anion, and Z is an alkali metal or alkaline cation, and is preferably represented by $$Cu^{+2}SO_4^{-2} + K^+I^- \rightarrow Cu°(+1, \text{ or } +2, \text{ also}) + K_2SO_4 + I_2.$$

The process may be performed where the two reactants are carried in a superabsorbent polymer. The solids carriers for the two reactants may also include compositions of the present that comprise superabsorbent or non-superabsorbent polymers, natural products (e.g., papers, cellulosic solids, water-insoluble porous materials which absorb or adsorb the film-forming material within the structure, water-soluble porous materials which absorb or adsorb the film-forming material within the structure, porous containers which merely slowly release a volume of the film-forming material, porous containers which both dissolve and physically release volumes of the film-forming composition through pores, and the like. In general, selection of an effective application rate can depend on habitat depth, surface debris, emergent and surface vegetation, organic matter, microbial and algal concentration, the specific target species, and the developmental stage of the target species. Superabsorbent polymers are described, by way of non-limiting examples in U.S. Pat. Nos. 6,403,674; 4,731,391. Superabsorbent polymers, including starch graft co-polymers, are known in the art. See, for example, those described in U.S. Pat. Nos. 4,375,535 and 4,497,930 (incorporated herein by reference), which have disclosed uses as adhesives, flocculants, sizes, water-retaining materials for agriculture and water-absorbing materials for sanitary materials. However, the spectrum of advantages attendant the use of superabsorbent polymers in solid and flowable terrestrial insecticidal, pesticidal or insecticidal/pesticidal delivery compositions have gone unrecognized.

The superabsorbent polymers of the present invention are synthetic organic polymers which are solid and hydrophilic, absorbing over 100 times their weight in water. These superabsorbent polymers are typically in a powder, granule, extruded, or flake form, adapted to be blended and/or agglomerated into any shape or form.

The superabsorbent polymers may be, for example, acrylamide alkali metal acrylate co-polymers; propenenitrile homo-polymers, hydrolyzed, alkali metal salts; polymers of propenamide and propenoic acid, alkali metal salts; hydrolyzed acrylonitrile co-polymers, and starch graft co-polymers and ter-polymers thereof. All of these are designed to be hydrophilic, absorbing over 100 times their weight in water. The resulting hydrophilic polymers can absorb from over one hundred to greater than about 5000, more typically around 500 to about 1,000, times their own weight in water (measured using distilled water, pH 7.5, 25, 760 mm Hg. absorption within about 30 seconds). However, the absorption or swelling capacity and absorption or swelling time typically varies with each specific superabsorbent polymer.

One class of superabsorbent polymers include combinations of a starch and organic monomers, oligomers, polymers, co-polymers or ter-polymers. They may be manufactured in a variety of ways, for example, the methods described in U.S. Pat. Nos. 4,375,535 and 4,497,930, and can be, for example, the product of grafting corn starch (amylopectin) with acrylonitrile (an acrylic monomer or oligomer). A second class of superabsorbent polymers includes combinations of acrylamide and acrylate polymers, co-polymers and ter-polymers.

The following examples are provided as prophetic or actually performed descriptions of formats for delivery of technology according to the descriptions of the present invention.

Land mass, such as soil and sand, can be contaminated by microbes in a number of manners. The most common manner of soil contamination is from improper handling or disposal of organic wastes and sewage. Excessive rainfall can also stress sewage systems, causing them to overflow and spill raw sewage over the land. Whatever the source of the microbial contamination, the danger to animal life can persist for extended periods of time and can severely affect both the medical and economic health of an area. It is therefore essential that methods and plans be developed that can treat a wide variety of microbial contaminations, and do so in a rapid manner and at acceptable costs. The problem has been that soil mediation or repair is far more complex and difficult than water purification techniques.

Water can be readily transported through pipes into treatment areas, through filters, or be loaded with chemistry that rapid spreads through the water system to attack microbes. Land mass can not be moved about as readily, and materials added to soil do not disperse as widely as materials added to aqueous systems. Materials added to soil for purposes of microbe reduction or elimination must not persist beyond their useful life and must not contribute a contamination effect themselves.

The technology described herein includes at least a process for reducing the microbial content in an environment. At least two reagents are provided (as described elsewhere herein) that react in the presence of water to form $I_2$ in the environment to provide a concentration in aqueous material in the environment of at least 5 or at least 10 parts per million $I_2$/water. At least one of the at least two reagents has a coating thereon that prevents atmospheric moisture (e.g., up to 100% relative humidity at 80° F., specifically at 60% relative humidity at 80° F.) from causing more than 5% of the reagents to react with each other to form $I_2$ when exposed for at least twelve hours to atmospheric moisture.

The technology disclosed herein is based in-part on the discovery that the provision of molecular iodine into microbially contaminated land mass (e.g., soil or sand) can mediate the land mass by killing or at least reducing the concentration of the vast majority of microbes that would ordinarily persist in the land mass.

Land mass (generally soil and/or sand) may become contaminated with any variety of microbes that may be harmful to vegetation or fauna that come into contact with the microbes. The land mass is then treated with molecular iodine in vapor or dissolved liquid form to provide a concentration in water or aqueous mass of at least about 10 parts per million. The molecular iodine (as opposed to iodide anion) is provided as a) a gas, b) liquid or c) provided as two reactants that form molecular iodide (s a gas or into a liquid) in the soil, either by using an aqueous carrier, water of hydration or ambient ground water. The source of molecular iodine may be topically applied, ploughed into the soil, mixed into the soil, injected into the soil, sprayed onto the soil, or otherwise applied where desired. Elemental iodine is a biocidally active form of iodine that has been used as a water disinfectant for almost a century. It is also widely used as a sanitizing compound in the food processing industry. Chlorine solution (especially hypochlorites) have been widely using by growers as a sanitizing wash for many fruits and vegetables. However, the strong oxidizing effect of chlorine in water with a moderate to high organic load results in a number of different complex compounds (trihalomethanes or THM) which can become a significant environmental hazard. There are strong reasons to minimize the excessive use of chlorine in the environment.

One way of providing molecular iodine ($I_2$) on site, rather than having to find a way of transporting it to a site) is to provide reactants that can readily produce molecular iodine on-site in a controllable reaction. One format of providing the molecular iodine would be through the oxidation-reduction reaction between two salts to produce the molecular iodine. It is a readily controlled environment where the reaction can be performed in an aqueous environment. One reaction that can effect this would be generically described as:

$$X^+Y^-+Z+I \longrightarrow X^\circ+Z^+Y^-+I_2$$

In this reaction scheme, X is a metal (preferably a multivalent metal and more particularly a divalent metal), Y is an anion (preferably a multivalent anion and more preferably a divalent anion, and an anion having at least two oxygen atoms), Z is an alkali metal or alkaline cation. Examples of X are copper, iron, manganese, lead, nickel, tin, and the like, Y can be sulfate, sulfite, sulfonate, carbonate, phosphate, phosphate, nitrate, nitrie, borate, and the like, and Z can be sodium, lithium, potassium, ammonium, magnesium, aluminum, and the like. One preferred reaction would be:

$$Cu^{+2}SO_4^{-2}+K^+I^- \rightarrow Cu^\circ(Cu^{+1} \text{ or } Cu^{+2})+K_2SO_4+I_2$$

This reaction takes place readily in an aqueous environment and produces molecular iodine at a controlled rate. The reaction may be used, as intimated above, by either causing the reaction to occur in a container and directing the iodide into the soil (as by gas injection) or by dissolving the molecular iodide and injecting or spraying the dissolved iodide into or onto the soil. The reaction may also be used by dispersing or mixing the two ingredients into the land mass, either with additional water provided, with water of hydration on the first reactant (e.g., $X^+Y^-.nH_2O$, such as $CuSO_4.5H_2O$) or with ambient water in the land mass. It is preferred in some embodiments that anhydrous cupric sulfate be used as even the presence of the hydrated water can remove protective coatings from the particles. Cupric sulfate or other metal components should therefore preferably have less than 5% hydrated component, less than 3% hydrated component, less than 1% hydrated component or between 0 and 0.5% hydrated component (water). The two reactants may be physically separated from each other before being combined for application or reaction, as in separate pouches or containers or individually coated particles. The two reactants may be provided in a solid carrier medium that separates the two reactants until they are in contact with water (as in a soluble carrier such as polyvinyl alcohol, gelatin, amylase, sugars and the like, in pellet or block form). The two reactants may be provided as liquids in separate containers to be mixed immediately before application. The two reactants may be independently coated with a soluble/dispersible coating and the two ingredients kept in a single water-tight container.

Individually coated particles can be provided in water-soluble containers/coverings by using water-soluble or water-dispersible coating materials that are also organic solvent soluble (alcohol soluble) such as PVA, gels, polyvinylpyrrolidone, silica coatings, poly(ether ketones), poly(ester ketones), and the like are applied to the individual particles (one single reagent) or groups of particles (both or all reagents) and prilled, spray dried, or otherwise dried into separate, agglomerated, or packed coated particles.

If provided in solid form (e.g., pellets, grains, tablets, powder, blocks, etc,), the solid is preferably mixed into the soil rather than merely spread on top of the soil or sand, so as to prevent winds from blowing the solid away or allowing the iodine to dissipate and evaporate from the environment without effectively penetrating the soil. If the solids are sufficiently large (e.g., at least 1.0 mm, preferably at least 2.0 mm in diameter), they can be more safely sprinkled on the surface of the soil or sand without as much concern of being blown away or unevenly distributed by the wind. The solids may be otherwise ploughed into the soil or sand, raked into the soil or sand, injected into the soil or sand, mixed with solid and sand and deposited onto the soil and sand or otherwise securely applied.

It will be apparent to one skilled in the art that there are various reactant chemicals that can be used. The reaction between anhydrous cupric sulfate and potassium iodine to produce iodine is one which is known in the art. Generally two parts (molecular stoichiometry) potassium iodine is required for every one part of anhydrous cupric sulfate to produce the desired reaction. In order to avoid problems in implementing the invention with the chemicals described above, the following matters should be noted. When using container or mixing prior to application, non-ferrous mixing containers and non-ferrous application instruments (or polymer coated ferrous material) should be used in order to avoid galvanic depositing of copper from solution. Application with absorbent and superabsorbent carriers (acrylic polymers, for example) has been found to require an additional amount of cupric sulfate over and above that used for the reaction. The reason for this is believed to be that the substrate has a tendency to sequester multivalent ions. With mixing in the vicinity of workers, care should be taken to consult safety data sheets relating to iodine gas before experimentation of any magnitude is conducted.

Soil microorganisms tend to congregate at the soil surface in a shallow layer of approximately 10 centimeters in depth. This shallow layer is referenced as either the weathering layer or the plough layer. The large majority of food (leaf fall, plant and animal detritus, etc.) is available at the soil surface. Natural biodegradation end products are fulvic and humic acids which may take up to 25-30 years to biodegrade. Microbial population size bears a direct relationship to the availability of food sources. A distribution of microorganisms may exist in the initial 75 centimeters of a soil profile and may include aerobic bacteria, anaerobic bacteria, actinomycetes, fungi, viruses, rickettsiae and algae. The total aerobic and anaerobic bacteria in the upper 8 cm of soil may be 77-80 percent of the total bacteria found in the 75 cm. profile. 95 percent of all bacteria may be found in the upper 25 cm. of the soil profile. Aerobic bacteria may average between 80-90 percent of the total bacteria for the soil horizons investigated. Thus it is desirable that the gas be provided through the major portions of this depth, e.g., at least to 8-25 centimeters.

Iodine is the preferred sanitizing agent in the food industry as it is acknowledged as a more effective user friendly sanitizing agent than chlorine. In addition, depending upon the concentrations, it is safe, can be effectively used at reduced concentrations (up to ten times less) than chlorine yet with a higher microbial kill rate. Iodine (unlike chlorine) does not produce any harmful substances such as carcinogens, and if nearly all by-products are removed, can produce an environmentally safe waste water. Being a solid at room temperatures and supplied, immersed in water, the potentially harmful effects of exposure to a concentrated sanitizing agent such as chlorine are removed, significantly improving environmental work conditions. Furthermore, iodine is less corrosive than chlorine reducing corrosive effects from the use of a biocide.

A number of United States patents disclose the use of iodine in conjunction with processes for purification of water. For example, U.S. Pat. No. 4,888,118 discloses a water purification process in which the water is passed through a mass of nylon 4 complex with iodine. The treated water is subsequently passed through nylon 4 to remove iodine from the water.

One of the difficulties with the known systems is to maintain an optimum amount of active iodine delivered into the target water supply for the specified purpose. To date there has been no effective system which can effectively and economically guarantee the delivery of exactly the right amount of active iodine at higher levels into the water used to wash produce in the case where iodine is used for food sanitization or into water delivered through reticulation networks, not only to prevent waste of iodine and economic loss but also to ensure that there is an acceptable minimum of active iodine.

Iodine recovery processes are known whose objective is to recover iodine to compensate for gradual reduction of $I_2$ in the flowing water and to provide a desired iodine residual. The process described in U.S. Pat. No. 5,176,836 is distinguished from previous systems by providing a continuous long term microbiological control process in a water supply particularly in space vehicle applications wherein $I_2$ is released into the water stream flowing through a suitable anion exchange resin.

Iodinated resin beds are known as a means for recharging a water supply with a minimum amount of active iodine. The recharging is effected by treatment with an aqueous iodine solution produced by flowing water through a bed of iodine crystals. The iodine residual is monitored and the bed recharged where necessary by adjusting the flow rate of water through the bed of iodine crystals. This is an expensive method of monitoring the level of active iodine and the resin rich in bound iodine is very expensive. In addition, the capacity of the resin is limited and reloading techniques in the field would be difficult to maintain in high water flow conditions. Also, this process is best suited to low level (<4 ppm) delivery of active iodine usually in a clean filtered water environment. This is due to the slow dissolving rate of iodine from known iodine beds and the limitation of the release rate and saturation of the anion exchange resins.

An ideal level of active iodine to be maintained in the aqueous content in the soil or sand is in the range of at least or greater then 10 ppm to 25 ppm although some applications may require higher concentrations. When iodine is used in large spill sanitizing applications, it may react with organic matter in which case the active iodine can be reduced to the point where there is little left for microbiological control. If resins (e.g., superabsorbing polymers) are used to deliver active iodine, this could necessitate continual monitoring of iodine concentration. It is expensive to use resin in large areas of soil, so it is likely that this mode of delivery would be used in more localized areas. Saturation of resin with 46% weight Iodine will produce around 4 ppm active iodine release, which is insufficient alone, but with the reactive mixture, higher concentrations of molecular iodine can be provided. A controlled iodine delivery process would be one in which the level of iodine can be maintained at a predetermined optimum level and without constant manual intervention and monitoring.

The process technology of the present disclosure may be practiced in a number of formats, such as a process for reducing the microbial content in land mass by providing molecular iodine in the land mass in a concentration in aqueous material in the land mass of at least 10 parts per million. The aqueous material should have a concentration of at least 10 parts per million is applied to the land mass. Specific formats include two reactants are added to the land mass and the two reactants react in the presence of water to generate a concentration of at least 10 parts per million in the water of the molecular iodine, especially where the two reactants are a) mixed with the land mass and at least some of the water present is ambient water; b) mixed with the land mass and at least some of the water present is water of hydration of one of the two reactants; c) mixed with the land mass and at least some of the water present is applied to the land mass at about the same time as the application of the two reactants; d) mixed with the land mass and at least one of the two reactants is coated to prevent premature reaction with water or another reactant. The process is particularly useful on recently contaminated sites, especially where the contaminant microbes reside in the top 25 cm of the soil such as where the land mass is sand at a site where organic waste matter has contaminated the san with microbes.

Among the ways of applying the molecular iodine are at least where molecular iodine gas is injected into the land mass; where the molecular iodine gas is generated in a closed container and injected into the land mass; where the land mass is physically disturbed to assist mixing of molecular iodine into the land mass; where physical disturbance comprises plowing of the land mass; and where solid reactant material to generate the molecular iodine is deposited in the land mass by the physical disturbance. The process may use the above reaction to form the molecular iodine represented by $$XY + ZI \rightarrow X° + ZY + I_2$$

wherein X is a metal, Y is an anion, Z is an alkali metal or alkaline cation, or where X is a multivalent metal, Y is a multivalent anion, and Z is an alkali metal or alkaline cation, and is preferably represented by $$Cu^{+2}SO_4^{-2} + K^+I^- \rightarrow Cu°(\text{and/or } Cu^{+1}) + K_2SO_4 + I_2.$$

The process may be performed where the two reactants are carried in another medium as described herein.

The concentration of the iodine forming material may be selected in the article according the ultimate needs and designs of the manufacturer, and the level of ant-bacterial effect desired. The concentration of the iodine gas in the liquid in the absorbent material is one measure of the desired results, and a further measure of the desired results is referred to in the art as the kill percentage, a measure of the percent of a specific bacteria (e.g., E. coli) in a liquid sample that would be killed in 5 minutes by the level of active ingredient present. An example would be that the presence of about 8 parts per million of gaseous iodine dissolved in the aqueous material in the absorbent material would have a kill percentage over 50%. It would be desired, as noted above, to have higher concentrations of gaseous iodine in the liquid so that kill percentages are at least 60%, at least 70%, at least 80% and even at least higher than 90% for targeted bacteria and other microbes. Depending upon the specific bacteria or microbe selected for the measurement, the liquid may have to be provided with at least 10 parts per million (ppm), at least 15 ppm, at least 20 ppm, or at least 25 ppm by controlling the amount of reagents added, the rate of reaction of the reagents, and other controls aimed at keeping the iodine in solution in the liquid, such as providing thickening agents or other materials that would reduce the volatility of the iodine gas from the solution.

Machine dishwasher products for household use are usually supplied in the form of powders or more recently also in the form of shaped bodies (tablets). The supply form of a liquid in this sector has hitherto only achieved minor importance on the market. Compared with the solid supply forms, liquids do, however, have advantages with regard to dosing and esthetic product advantages which should not be underestimated, which make this supply form of interest. For example, there is already broad prior art both with regard to nonaqueous, for the most part solvent-based, but also with regard to aqueous dishwashing products for washing dishes in a customary domestic dishwashing machine.

For example, DE 20 29 598 describes liquid cleaning compositions which comprise 14 to 35% by weight of sodium tripolyphosphate, 0.1 to 50% by weight of a potassium and/or ammonium salt of an inorganic or organic acid, water, and optionally surfactants, solubility promoters, sequestrants, persalts and other ingredients.

Linear-viscoelastic cleaning compositions for machine dishwashing are also described in European patent application EP 446 761 (Colgate). The compositions disclosed here comprise up to 2% by weight of a long-chain fatty acid or a salt thereof, 0.1 to 5% by weight of surfactant, 5 to 40% by weight of water-soluble builders, and up to 20% by weight of chlorine bleaches and a polycarboxylate thickener, where the ratio of potassium ions to sodium ions in these compositions should be 1:1 to 45:1.

Machine dishwasher products in the form of clear, transparent gels are disclosed in European patent application EP 439 878 (Union Camp Corp.). The compositions described therein comprise a polyacrylate thickener, which forms a gel matrix with water, surfactant, bleach, a builder and water. Machine dishwasher products in the form of gels are also described in European patent application EP 611 206 (Colgate). These compositions comprise 1 to 12% by weight of a liquid nonionic surfactant, 2 to 70% by weight of builders, and enzymes and a stabilization system which is composed of swelling substances and hydroxypropylcellulose.

Viscoelastic, thixotropic dishwashing products comprising 0.001 to 5% by weight of surfactant, and enzymes and an enzyme stabilization system of boric acid and polyhydroxy compounds are described in international patent application WO 93/21299 (Procter & Gamble). The products disclosed therein likewise comprise 0.1 to 10% by weight of one or more thickeners.

Dishes washed by machine are nowadays often subject to higher requirements than dishes washed manually. For example, even dishes which have been completely cleaned of food residues will not be evaluated as being perfect if, after machine dishwashing, they still have whitish marks based on water hardness or other mineral salts which, due to a lack of wetting agents, originate from dried-on water drops.

In order to obtain sparkling and stain free dishes, rinse aids are therefore nowadays used with success. The addition of rinse aid at the end of the wash program ensures that the water runs off from the ware as completely as possible, so that the various surfaces are residue-free and sparkling at the end of the wash program.

Machine dishwashing in domestic dishwashing machines usually includes a prewash cycle, a main wash cycle and a clear-rinse cycle, which are interrupted by intermediate rinse cycles. With most machines, the prewash cycle for heavily soiled dishes can be selected, but is only chosen by the consumer in exceptional cases, meaning that in most machines a main wash cycle, an intermediate rinse cycle with clean water and a clear-rinse cycle are carried out. The temperature of the main wash cycle varies between 40 and 65° C., depending on the type of machine and program choice. In the clear-rinse cycle, rinse aids are added from a dosing chamber in the machine; these usually comprise nonionic surfactants as the main constituent. Such rinse aids are in liquid form and are described widely in the prior art. Their function is primarily to prevent limescale marks and deposits on the washed dishes.

These so-called "2 in 1" products lead to simplified handling and remove the burden from the consumer of the additional dosing of two different products (detergent and rinse aid). Nevertheless, to operate a domestic dishwashing machine, two dosing operations are periodically required since the regeneration salt must be topped up in the water softening system of the machine after a certain number of wash operations. These water softening systems consist of ion exchanger polymers which soften the hard water flowing into the machine and, after the wash program, are regenerated by rinsing with salt water.

Products which, in the form of so-called "3 in 1" products, combine the conventional detergents, rinse aids and a salt replacement function have recently been described in the prior art. These products are, however, only available as solids (tablets).

The present technology with the iodine generating materials therein can provide a product which is pourable and can thus be readily and freely dosable in terms of amounts and which only has to be dosed once per use without the dosing of another product and thus a duplicate dosing operation being necessary even after a relatively high number of wash cycles. The aim was to provide a liquid to gel-like product which, in addition to the "incorporated rinse aid", renders it unnecessary to top up the regeneration salt container and thus further simplifies handling. In this connection, the performance of the product was to reach or exceed the level of performance of conventional three-component product dosings (salt-detergent-rinse aid) or of new types of two-component product dosings ("2 in 1" detergent-rinse aids). In this connection, the products to be provided should be superior to conventional products with regard to as many properties as possible. In particular, the dichotomy which arises in the case of many pourable products—advantages with certain properties (flowability, ability to be removed completely, pleasing product appearance etc.) are accompanied by disadvantages with other properties (settling behavior, storage stability, performance etc.)—should be overcome. The object was therefore also to provide products which combine advantageous rheological properties (flowability, ability of the remainder to be removed etc.), advantageous product characteristics (appearance, cleaning power, storage stability etc.) and a production which can be realized industrially without problems and can be carried out in a cost-effective manner.

U.S. Pat. No. 7,192,911 describes a non-aqueous machine dishwasher product comprising: a) 1 to 60% by weight of nonaqueous solvent(s), b) 0.1 to 70% by weight of copolymers of i) unsaturated carboxylic acids ii) monomers containing sulfonic acid groups iii) optionally further ionic or non-ionogenic monomers c) 5 to 30% by weight of nonionic surfactant(s). Published US Patent Application No. 20040167048 similarly discloses an aqueous Three-in-One dishwasher composition. Also, the machine dishwasher product can be packaged in portions in a water-soluble enclosure. This Patent and this Patent Applications (Sunder et al.) are incorporated herein in its entirety to assist in the disclosure of dishwashing compositions and delivery systems that can be used in conjunction with the iodine delivery compositions, components and systems of the present technology. Among the packet or package delivery systems of this patent are wrapped compositions, packets with multiple chambers for different compositions, and solvent or liquid carriers that do not destroy the water-soluble or water-dispersible film carriers such as the water-soluble polymer material which partially or completely surrounds the nonaqueous liquid dishwasher product is a water-soluble packaging. This is understood as meaning a flat component which partially or completely surrounds the nonaqueous liquid dishwasher product. The exact shape of such a packaging is not critical and can be adapted largely to the use conditions. For example, processed plastic films or sheets, capsules and other conceivable shapes worked into different shapes (such as tubes, sachets, cylinders, bottles, disks or the like) are suitable.

According to the invention, particular preference is given to films which can be adhered and/or sealed, for example, to give packagings such as tubes, sachets or the like after they have been filled with part portions of the cleaning compositions according to the invention or with the cleaning compositions according to the invention themselves.

Also preferred according to the invention are plastic film packagings made of water-soluble polymer materials due to the properties which can be matched in an excellent manner to the desired physical conditions. The water-soluble or water-dispersible materials described below can be used as the water-soluble or water-dispersible components in all aspects of the practice of the present technology, including the separation of iodine-forming reactive ingredients.

Such films are known in principle from the prior art. In summary, hollow bodies of any shape, which can be produced by injection molding, bottle blowing, deep-drawing etc., and also hollow bodies made of films, in particular pouches, are preferred as packagings for portioned products according to the invention. Preferred liquid aqueous machine dishwasher products according to the invention are thus characterized in that the water-soluble enclosure comprises a pouch made of water-soluble film and/or an injection-molded section and/or a blow-molded section and/or a deep-drawn section.

It is preferred for one or more enclosure(s) to be sealed. This brings with it the advantage that the nonaqueous liquid dishwasher products are optimally protected against environmental influences, in particular against moisture. In addition, by virtue of these sealed enclosures, it is possible to further develop the invention inasmuch as the cleaning compositions comprise at least one gas to protect the contents of the enclosure(s) against moisture, see below.

Suitable materials for the completely or partially water-soluble enclosure are in principle all materials which are completely or partially soluble in aqueous phase under the given conditions of a washing operation, rinsing operation or cleaning operation (temperature, pH, concentration of washing-active components). The polymer materials may particularly preferably belong to the groups consisting of (optionally partially acetalized) polyvinyl alcohol, polyvinylpyrrolidone, polyethylene oxide, gelatin, cellulose and derivatives thereof, starch and derivatives thereof, in particular modified starches, and mixtures (polymer blends, composites, coextrudates etc.) of said materials. Particular preference is given to gelatin and polyvinyl alcohols, and said two materials in each case in a composite with starch or modified starch. Inorganic salts and mixtures thereof are also suitable materials for the at least partially water-soluble enclosure.

Preferred liquid aqueous machine dishwasher products according to the invention are characterized in that the enclosure comprises one or more materials from the group consisting of acrylic acid-containing polymers, polyacrylamides, oxazoline polymers, polystyrene-sulfonates, polyurethanes, polyesters and polyethers and mixtures thereof.

Particularly preferred liquid aqueous machine dishwasher products according to the invention are characterized in that the enclosure comprises one or more water-soluble polymer(s), preferably a material from the group consisting of (optionally acetalized) polyvinyl alcohol (PVAL), polyvinylpyrrolidone, polyethylene oxide, gelatin, cellulose, and derivatives thereof and mixtures thereof, more preferably (optionally acetalized) polyvinyl alcohol (PVAL).

Standard commercial polyvinyl alcohols, which are supplied as white-yellowish powders or granules with degrees of polymerization in the range from about 100 to 2500 (molar masses from about 4000 to 100 000 g/mol), have degrees of hydrolysis of 98-99 or 87-89 mol % and thus also contain a residual content of acetyl groups. The polyvinyl alcohols are characterized on the part of the manufacturers by stating the degree of polymerization of the starting polymer, the degree of hydrolysis, the hydrolysis number and the solution viscosity.

Depending on the degree of hydrolysis, polyvinyl alcohols are soluble in water and less strongly polar organic solvents (formamide, dimethylformamide, dimethyl sulfoxide); they are not attacked by (chlorinated) hydrocarbons, esters, fats and oils. Polyvinyl alcohols are classified as being toxicologically acceptable and at least some of them are biodegradable. The solubility in water can be reduced by after-treatment with aldehydes (acetalization), by complexation with Ni or Cu salts or by treatment with dichromates, boric acid or borax. The coatings made of polyvinyl alcohol are largely impenetrable to gases such as oxygen, nitrogen, helium, oxygen, carbon dioxide, but allow water vapor to pass through.

For the purposes of the present invention, it is preferred that the enclosure comprises a polyvinyl alcohol whose degree of hydrolysis is 70 to 100 mol %, preferably 80 to 90 mol %, particularly preferably 81 to 89 mol % and in particular 82 to 88 mol %. As materials for the enclosure, preference is given to using polyvinyl alcohols of a certain molecular weight range, it being preferred according to the invention for the enclosure to comprise a polyvinyl alcohol whose molecular weight is in the range from 10,000 to 100,000 $\mu mol^{-1}$, preferably from 11,000 to 90,000 $\mu mol^{-1}$, particularly preferably from 12,000 to 80,000 $\mu mol^{-1}$ and in particular from 13,000 to 70,000 $\mu mol^{-1}$.

The degree of polymerization of such preferred polyvinyl alcohols is between approximately 200 to approximately 2100, preferably between approximately 220 to approximately 1890, particularly preferably between approximately 240 to approximately 1680 and in particular between approximately 260 to approximately 1500.

The polyvinyl alcohols described above are commercially available widely, for example under the trade name Mowiol™ (Clariant). Polyvinyl alcohols which are particularly suitable for the purposes of the present invention are, for example, Mowiol™ 3-83, Mowiol™ 4-88, Mowiol™ 5-88 and Mowiol™ 8-88.

Polyvinyl alcohol may be coated on particles (even water s-oluble particles as used in the present technology) by use of particle coating technologies such as particle impacting in a fluidized bed or equivalent equipment such as shown in U.S. Pat. No. 6,037,019 (Kooyer).

The solubility of PVAL in water can be changed by after-treatment with aldehydes (acetalization) or ketones (ketalization). Polyvinyl alcohols which have proven to be particularly preferred and particularly advantageous due to their outstandingly good solubility in cold water are those which are acetalized or ketalized with the aldehyde or keto groups, respectively, of saccharides or polysaccharides and mixtures thereof. It has proven especially advantageous to use the reaction products of PVAL and starch. In addition, the solubility in water can be changed by complexation with Ni or Cu salts or by treatment with dichromates, boric acid, borax and thus be adjusted to desired values in a targeted manner. Films made of PVAL are largely impenetrable to gases such as oxygen, nitrogen, helium, hydrogen, carbon dioxide, but allow water vapor to pass through. Examples of suitable water-soluble PVAL films are the PVAL films obtainable under the name "SOLUBLON®" from Syntana Handelsgesellschaft E. Harke GmbH & Co. Their solubility in water can be adjusted to a precise degree and films of this product series are available which are soluble in the aqueous phase in all temperature ranges relevant for the application.

Polyvinylpyrrolidones, shortened to PVPs, are prepared by free-radical polymerization of 1-vinylpyrrolidone. Standard commercial PVPs have molar masses in the range from about 2500 to 750,000 g/mol and are supplied as white, hygroscopic powders or as aqueous solutions.

Polyethylene oxides, shortened to PEOXs, are polyalkylene glycols of the general formula H—[O—CH$_2$—CH$_2$]$_n$—OH which are prepared industrially by base-catalyzed polyaddition of ethylene oxide (oxirane) in systems comprising mostly small amounts of water with ethylene glycol as starter molecule. They have molar masses in the range from about 200 to 5,000,000 g/mol, corresponding to degrees of polymerization n of from about 5 to >100 000. Polyethylene oxides have an extremely low concentration of reactive hydroxy end groups and exhibit only weak glycol properties.

Gelatin is a polypeptide (molar mass: about 15,000 to >250,000 g/mol) which is obtained primarily by hydrolysis of the collagen present in animal skin and bones under acidic or alkaline conditions. The amino acid composition of the gelatin largely corresponds to that of the collagen from which it has been obtained and varies depending on its provenance. The use of gelatin as water-soluble shell material is extremely widespread in particular in pharmacy in the form of hard or soft gelatin capsules. Gelatin is not used widely in the form of films due to its high cost relative to the polymers specified above.

For the purposes of the present invention, preference is also given to liquid dishwasher products whose packaging consists at least partially of water-soluble film of at least one polymer from the group consisting of starch and starch derivatives, cellulose and cellulose derivatives, in particular methylcellulose and mixtures thereof.

Starch is a homoglycan, where the glucose units are .alpha.-glycosidically joined. Starch is made up of two components of different molecular weight: from about 20 to 30% of straight-chain amylose (MW about 50 000 to 150 000) and 70 to 80% of branched-chain amylopectin (MW about 300,000 to 2,000,000). In addition, small amounts of lipids, phosphoric acid and cations are also present. Whereas the amylose forms long, helical, intertwined chains with about 300 to 12 000 glucose molecules as a result of the bond in the 1,4 position, the chain in the case of amylopectin branches after on average 25 glucose building blocks by a 1,6 bond to a branch-like structure with about 1500 to 1200 molecules of glucose. As well as pure starch, starch derivatives which are obtainable from starch by polymer-analogous reactions are also suitable for the preparation of water-soluble enclosures for the washing product, rinse product and cleaning product portions for the purposes of the present invention. Such chemically modified starches include, for example, products from esterifications or etherifications in which hydroxy hydrogen atoms have been substituted. However, starches in which the hydroxy groups have been replaced by functional groups which are not bonded via an oxygen atom can also be used as starch derivatives. The group of starch derivatives includes, for example, alkali metal starches, carboxymethyl-starch (CMS), starch esters and starch ethers, and aminostarches.

Pure cellulose has the formal gross composition $(C_6H_{10}O_5)_n$ and considered formally, is a .beta.-1,4-polyacetal of cellobiose which, for its part, is constructed from two molecules of glucose. Suitable celluloses consist of about 500 to 5000 glucose units and, accordingly, have average molar masses of from 50,000 to 500,000. Cellulose-based disintegrants which can be used for the purposes of the present invention are also cellulose derivatives which are obtainable from cellulose by polymer-analogous reactions. Such chemically modified celluloses include, for example, products of esterifications and etherifications in which hydroxyl hydrogen atoms have been substituted. However, celluloses in which the hydroxy groups have been replaced by functional groups not attached via an oxygen atom may also be used as cellulose derivatives. The group of cellulose derivatives includes, for example, alkali metal celluloses, carboxymethylcellulose (CMC), cellulose esters and ethers, and aminocelluloses.

Preferred enclosures of at least partially water-soluble film comprise at least one polymer with a molar mass between 5,000 and 500,000 g/mol, preferably between 7,500 and 250,000 g/mol and in particular between 10 000 and 100 000 g/mol. The enclosure has different material thicknesses depending on the production process, preference being given to liquid aqueous machine dishwasher products according to the invention in which the wall thickness of the enclosure is 10 to 5,000 μm, preferably 20 to 3000 μm particularly preferably 25 to 2,000 μm and in particular 100 to 1,500 μm. If film pouches are chosen as packaging, then the water-soluble film which forms the enclosure preferably has a thickness of from 1 to 300 μm, preferably from 2 to 200 μm, particularly preferably from 5 to 150 μm and in particular from 10 to 100 μm.

These water-soluble films can be produced by various production processes. In principle, blowing, calendering and casting processes should be mentioned. In a preferred process, the films are blown starting from a melt using air by means of a blowing mandrel to give a hose. In the calendering process, which is likewise a type of preferred production process, the raw materials plasticized by suitable additives are atomized to form the films. It may in particular be necessary here to follow the atomization with a drying step. In the casting process, which is likewise a type of preferred production process, an aqueous polymer preparation is placed onto a heatable drying roll, is optionally cooled following evaporation of the water and the film is removed in the form of a sheet. Where necessary, this sheet is additionally powdered before being removed or whilst being removed.

The technology described herein includes q process for reducing the microbial content in an environment comprising providing at least two reagents that react in the presence of water to form $I_2$ in the environment to provide a concentration in aqueous material in the environment of at least 5 parts per million $I_2$/water, at least one of the at least two reagents having a coating thereon that prevents atmospheric moisture from causing more than 5% of the reagents to react with each other to form $I_2$ when exposed for twelve hours to atmospheric moisture. The technology may also be described as process for reducing the microbial content in land mass comprising providing molecular iodine gas or at least two reagents that react in the presence of water to form $I_2$ in the land mass to provide a concentration in aqueous material in the land mass of at least 5 parts per million $I_2$/water. Preferably the aqueous material has a concentration of $I_2$ as at least 10 parts per million is applied to the land mass. The process may include two reactants added to the land mass and the two reactants react in the presence of water in or on the land mass to generate a concentration of at least 10 parts $I_2$ per million in the water. At least some of the water present may be ambient water, or at least some of the water present may be applied to the land mass at about the same time as the application of the two reactants. The process may have the two reactants mixed with the land mass and at least one of the two reactants is coated with a water soluble or water-dispersible coating to prevent premature reaction with atmospheric moisture or another reactant. The process may cause molecular iodine gas to be generated at a soil site and then injected into the land mass. The land mass may be physically disturbed to assist mixing of molecular iodine into the land mass so as to apply solid reactant material to generate the molecular iodine by depositing it in the land mass by the physical disturbance.

The technology of the present invention also includes a process for reducing the microbial content in a confined area comprising providing at least two reagents that react in the presence of water to form $I_2$ into the confined area and providing water to provide a concentration in aqueous material in vapor or liquid within the confined area of at least 10 parts per million $I_2$/water. At least 50% or 75% of total stoichiometric $I_2$ formed in the confined area can remain in the refined area for at least 2 minutes. The process may be practiced where at least one of the two reagents that react to form $I_2$ is provided into the confined area with a covering of a water-soluble or water-dispersible material. The at least two reagents that react to form $I_2$ may be provided into the confined area within a packet or covering comprising a water-soluble or water-dispersible material. Additional active agents, other than the at least two reagents, may be provided within the packet or covering, and there are at least two separate compartments within the packet or covering containing different reagents or an additional active agent Other technology described herein includes a process for reducing the microbial content in contact material placed against organs (especially skin) of patients comprising providing at least two reagents that react in the presence of water to form $I_2$ in the contact material to provide a concentration in aqueous material in the contact material of at least 10 parts per million $I_2$/water. The reagents further comprise at least one halogen-providing compound selected from the class consisting of iodates, chlorates, bromates, periodates, perchlorates and perbromates. The articles and methods and compositions described herein for the use in environments activated by water are also useful in environments for activation by compositions comprising alcohols, as described above, with little or no modification of the structures and compositions, as also described herein. For example, the present technology may include a method of inhibiting microbial growth on an article comprising providing a composition on the article, the composition comprising at lest two compounds that react in the presence of water and/or alcohol to produce molecular iodine, and providing the composition on the article in the presence of a liquid comprising an alcohol; such as a C1 to C6 alcohol. Upon addition of the alcohol in an amount of between 10 and 100% by weight of the composition, a concentration of at least 5 parts per million of iodine is produced in the alcohol in less than 5 minutes. Particularly useful articles would include a surface wipe, hand-wipe, wiping pad, mop head, diaper, sponge, sanitary pad, bandage or wrap. The method may include the article comprising a fabric material and wherein water and/or alcohol absorbing material comprising fibers is provided in a same layer as the composition. The system wherein at least one of the reactants is coated to provide protection against ambient moisture and humidity is again preferred.

EXAMPLES

Example 1

In a first experiment, a natural sample from Santa Monica beach was user. This soil sample was taken from an area close to a storm drain. Concentrations started at 1100 MPN enterococci per 100 gram sediment were used. Wash samples having a concentration of greater than 10 parts per million were used on the soil samples. Enterocci concentrations approached zero for all of five consecutive washes. A longer term experiment was then performed with sand dosed with a pure culture of enterococci, the >10 ppm iodine solution imbibed in the soil, and then autoclaving. The bacterial level started at 1050 MPN/100 g, and went to zero immediately upon treatment. This was clearly evidenced in five washes (all zero). Two samples were treated with >10 ppm iodine solutions and left to sit on the roof for several days. The bacterial levels were approximately zero at the end of the experiment. Samples that were imbibed with the >10 ppm solution and the sand raked, had bacterial levels that decreased in concentration during the days, and rebounded at night for two nights, and then ended up at zero, indicating effectiveness of the solution, and a benefit to combination of the solution with heat and/or light. The undisturbed controls in both dark and light ended up with countable bacteria.

Example 2

Prophetic

Particles of KI would be impact coated with smaller particles (1/10 to 1/5 diameter ratio) of polyvinyl alcohol in accordance with the teachings of the processes and equipment shown in U.S. Pat. No. 6,037,019 (Kooyer). These PVA coated particles could then be mixed with particles of cupric sulfate with no concern for any immediate reaction between the salts, even in the presence of ambient moisture.

The activity of the materials may be increased with respect to halogen releasing ability and volume by adding further halogen releasing components, especially iodates, chlorates, bromates, periodates, perchlorates and/or perbromates as a further reagent (e.g., as above 0% oe 0.5% to 200% by weight of the further halogen-releasing components to KI. Metal, non-metal, alkaline and alkali halogens compounds may be used.

The treatment may include use on mass water treatment (ponds or small lakes), continuous water treatment (in an enclosed flow stream where contact can be maintained in pipes or aqueducts for extended time periods), batch water treatment (in a tank), municipal water supplies, local residence (houses, hotels, town homes, condominiums and apartments), pools and aquatic facilities, and the like.

Example 3

Partial Prophetic

In this example, particles of KI and particles of copper sulfate are separately coated in water-removable coating materials comprising hydrophobic fumed silica (e.g., 0.1-0.5 microns, although other optional materials include cellulose fibers, lipids, water-softenable waxes, and sugars may be applied with non-aqueous solvents to avoid dissolution of the iodide or sulfate or the like. The separate coated particles might then be carried to an water drain site, the interior surface of the water drain (with biofilm deposits thereon) are pigged with a polyurethane pig under 1000 mm Hg pressure) so that the biofilm is partially disrupted and the particles contemporaneously or subsequently dusted onto the disrupted biofilm surface of the interior of the pipe (either immediately before, during or immediately after disruption).

Iodine gas and/or iodine dissolved in water would be generated at concentrations necessary for biocide applications upon the introduction of water (precipitation, direct addition, or from existing ambient moisture in the soil).

Example 3

Partial Prophetic

In a partial prophetic example, particles of KI were actually blended with 5% by weight Cab-O—Sil™ TG 709F hydrophobic fumed silica and blended together for a minimum of 30 seconds. This caused a layer of hydrophobic silica stand off particles to form a discontinuous layer on the KI surface. Old Bridge Chemicals $CuSO_4$ pentahydrate powder was also used but not treated with silica. Raw materials were mixed in the following ratio of 14.3 wt % active $CuSO_4$ and 85.7 wt % active KI. Upon intimate mixing this mixture does not show any discoloration or indication of reaction (iodine release) upon storage in 100% RH environment despite the close proximity of the intimately blended chemical reagent particles.

This mixture of reagents prophetically would be carried to a water drainage system site, the biofilm coating on the interior surface of the water drainage system, rain runoff pipe disrupted and the particles contemporaneously sprayed onto the interior disrupted surface (either immediately before, during or immediately after scraping of the interior surface of the pipe along its length). Iodine gas and/or iodine dissolved in water is generated at concentrations necessary for biocide applications upon the introduction of water (precipitation, direct addition, or from existing ambient moisture in the system).

Example 4

Prophetic

A prophetic example with a rain drain system having a seventy-inch interior diameter was provided with a pigging system and pressurizing system such as those available according to the teachings of U.S. Pat. Nos. 7,000,280; 6,067, 682; 5,924,158; 5,903,946; 5,384,929; and 5,265,302. The interior of the pipe surface, after being treated with such pigging systems, has at least some of the biofilm disrupted by the pigging and attendant scraping action of the pigs, so that the film is sufficiently disrupted as to readily enable penetration by liquids and gases.

Either attached to a rear end of a pig or in a trailing device (either pressure motivated or self powered (as with an electric motor robot) is a simple spraying system having a carried source of reactants and/or a feed system from an exterior source of reactants and water. For example, a single container of mixed coated particles of copper sulfate and potassium iodide can be carried in the robot and a hose providing water is connected to the robot to provide an exterior source of liquid. The solids can be fed into a mixing area and the water fed into that same mixing area, and the combination of solids (now having their coatings dissolved, which also tends to render them somewhat tacky, so as to facilitate adherence to the interior of the carrier surface) and water is sprayed onto the pipe or drain (water carrier) surface. This spraying may be done by conventional nozzles of sufficient size as to not get clogged by the carried solids and using the pressure from the water feed to spray the solution/dispersion/suspension of solids and water. It is preferred that a swiveling head be provided to assure coverage of the interior surface. It is to be noted that lower areas of the drain will be covered by runoff of liquid or the gases will disperse in the environment and contact all surfaces.

For shorter distances between the entry into the system and the points of film disruption and iodine application, it would be easy to mix materials outside of the system, transport them to the points of application, and then spray the mass without having to carry the iodine reactants themselves on the robot. By using a tackifying, slowly dissolving removable reactant coating on the particles, larger distances of application can be effected, as the reagents will adhere in the applied areas and the local presence of water will continue the iodine releasing action at the appropriate location.

Alternative disrupting means can be the hole/tunnel drilling systems with three overlapping rotating drill heads that revolve as well as rotate to provide a generally circular drilling format. The individual drill bits (e.g., the three symmetrical drill bits typically used) are also movable or adjustable radially to comport to the variations in the dimensions of the interior of the pipe and also any joints. By setting a maximum radial extension to a centimeter less than the actual minimum interior dimension of the pipe, thick biofilm can be assured of disruption without fear of causing significant damage to the pipe itself by the drill bit. Additionally, rather than the iron nitride or diamond drill bits used for tunneling, softer drill bits can be used that will abrade or disrupt the biofilm coating, but will not readily damage the pipe material.

A laser system (e.g., pulsed excimer laser may be used with the laser beam transmitted and the redirected in all directions within the interior of the drain) may also be used for physical disruption. Chemical means may be used to physically disrupt the biofilm, but reducing the chemical input into the drain is highly advantageous. Even within the present system the capture, filtering or other means of removing precipitated metals (e.g., the copper iodide) is desirable and may be required.

Example 5

Prophetic

Particles of KI would be impact coated with smaller particles (1/10 to 1/5 diameter ratio) of polyvinyl alcohol in accordance with the teachings of the processes and equipment shown in U.S. Pat. No. 6,037,019 (Kooyer). These PVA coated particles could then be mixed with particles of cupric sulfate with no concern for any immediate reaction between the salts, even in the presence of ambient moisture. These particles could be carried to the application site for admixture into water to provide iodine or into other carrier material for application to conduit surfaces. It is important to appreciate that both water-borne iodine and vapor-borne iodine can be produced in a single environment to address cracks, nooks and crannies in the delivery system where intimate contact with water might be difficult.

Example 6

Prophetic

Fibers would be extruded in a non-aqueous solvent of polyvinyl alcohol in two separate batches in combination with particulate reactants. One set of fibers would comprise 40% by weight of Copper Sulfate and the other set of fibers would comprise 40% by weight of Potassium Iodide. The two separate fibers would blended as 5% by total weight of fabric material into the fiber filled used in a diaper. The relatively low concentration (5%) of total added fiber would be expected to minimally change the properties expected from the fiber fill, except for the additional antimicrobial function. Upon activation by alcohol and/or water into the fibers, the polyvinyl alcohol would dissolve, the two reactants would dissolve in a single solution, the reactants would react, and the gaseous iodine would be produced.

The composition of the present technology provides a local concentration (in the water) of at least 5 ppm and preferably at least 10 parts per million iodine in water carried by the material (that is actual water and/or alcohol supported by the water absorbent material) when the material has 5% by weight of water and/or alcohol present in the water absorbent. The 5% is with respect to the total weight of water to the water absorbent material. The water and/or alcohol absorbing material preferably comprises water absorbing fibers. When providing alcohol, there is usually about 8% water present because of the difficulty in separating water from alcohol, except by expensive processing. The alcohol itself can provide additional anti-microbial activity, so thje combination of alcohol and the molecular iodine is particularly effective in the practice of the present technology.

The composition that reacts with water and/or alcohol to form molecular iodine may comprise at least two salts, one of which at least two salts comprises an iodide salt. The at least two salts may be selected from the groups consisting of a) XY and b) Z I, wherein X is a metal, Y is an anion, and Z is an alkali metal, ammonium or alkaline cation. X is preferably a divalent metal cation. Y is preferably selected from carbonate, sulfate, sulfite, phosphate, phosphate, nitrate and nitrite, and Z is preferably selected from the group consisting of lithium, potassium, calcium, magnesium, sodium and ammonium. The composition that reacts with water to form molecular iodine preferably comprises cupric sulfate and potassium iodide.

The articles and compositions may have the iodine forming composition appropriately located within the article. For example, where the article is a hand-wipe sheet or diaper, it may have more than 70% of total composition in a central 50% of volume of the diaper. There is little need for antimicrobial activity on the portions of the diaper contacting the outer portions of the hips. Similarly, there would be little need for such activity along the waistband of the diaper. It is therefore desirable to concentrate the active materials in the diaper where the water (e.g., urine) is likely to be emitted. The iodine would migrate through the path of the water to all wetted areas.

A method of inhibiting microbial growth in an article provides a composition within the article, the composition comprising at lest two compounds that react in the presence of water to produce molecular iodine, and placing the article against the skin of an animal where an aqueous emission from the animal may occur. The method acts so that upon addition of water in an amount of between 10 and 100% by weight of the composition, a concentration of at least 10 parts per million of iodine is produced in the water in less than 15 minutes. The activity of the materials may be increased with respect to halogen releasing ability and volume by adding further halogen releasing components, especially iodates, chlorates, bromates, periodates, perchlorates and/or perbromates as a further reagent (e.g., as above 0.1% to 200% by weight of the further halogen-releasing components to KI. Metal, nonmetal, alkaline and alkali halogens compounds may be used.

Another improvement would be to include starch materials into the composition or the surface to be treated so that the released iodine would cause the standard reaction for starch testing and a blue coloration would appear on the surface to alert caregivers that activation had occurred.

Example 7

Prophetic

Two porous films of water-soluble or water-dispersible material such as mannitol would be extruded, the porosity provided by mechanical punching of the film of leaching of materials from the film, as well understood in the art. The separate films would contain 40% by weight of Copper Sulfate and 40% by weight of Potassium Iodide. The films can be used as adjacent or opposite side containers for the fiber fill (preferably with a separate non-dissolvable film).

Example 8

Prophetic

Individual granules of Copper Sulfate and Potassium Iodide are coated with water-soluble/dispersible coatings, preferably in the 2-8 micron thickness range. The uncoated particles would preferably have a diameter of between 5-50 microns so that they could be carried in fiber fill for a diaper without too ready settling out of the fiber fill. The coated particles are mixed into the fiber fill, either alone or with a tacky material (on the fiber or on the particles, such as a partially dried coating on the particles) to avoid separation. The fiber particle blend would constitute the fiber fill in a diaper.

FIG. 1 shows a view of the inside of an opened diaper product 20 and the distribution of compositions according to the present technology. The diaper product 20 is shown with a longitudinal center-line 100 and a horizontal center-line 110 about which are approximately symmetrically disposed wide panels 30, adhesive tabs 40, a central absorbent sheet 24, a stretchable/flexible outer cover layer 32 that may be continuous with the wide panels 30. A sectioned area 26 exposes longitudinal elastic filaments 54 that form the elasticity of the diaper along with the crinkling pattern 52. There are significant indentations 50 on the sides of the diaper t20 to allow fitting to legs. The central absorbent sheet 24 is shown with four separate areas 22 within which there could be the heaviest concentrations of the iodine forming material, and two panels 34 that are towards a more rearward placement on a user where lower concentrations of iodine forming material could be located. Areas outside the central absorbing sheet 24 may have little or no iodine forming materials therein. As noted above, the concentration of the iodine forming materials should be centralized where liquids are more likely to be emitted into the absorbent area and be retained in the absorbent area. The upper region of the diaper and pad 36 and the lower region of the diaper and pad 38 could therefore have less total amount and less concentration of the iodine forming materials then the central area 37. These concentration variations in the vertical direction may also be reflected or substituted with similar regional variations in the horizontal direction of the diaper 20. The concentration of the iodine forming material may be selected in the article according the ultimate needs and designs of the manufacturer, and the level of antbacterial effect desired. The concentration of the iodine gas in the liquid in the absorbent material is one measure of the desired results, and a further measure of the desired results is referred to in the art as the kill percentage, a measure of the percent of a specific bacteria (e.g., *E. coli*) in a liquid sample that would be killed in 5 minutes by the level of active ingredient present. An example would be that the presence of about 8 parts per million of gaseous iodine dissolved in the aqueous material in the absorbent material would have a kill percentage over 50%. It would be desired, as noted above, to have higher concentrations of gaseous iodine in the liquid so that kill percentages are at least 60%, at least 70%, at least 80% and even at least higher than 90% for targeted bacteria and other microbes. Depending upon the specific bacteria or microbe selected for the measurement, the liquid may have to be provided with at least 5 or 10 parts per million (ppm), at least 15 ppm, at least 20 ppm, or at least 25 ppm by controlling the amount of reagents added, the rate of reaction of the reagents, and other controls aimed at keeping the iodine in solution in the liquid, such as providing thickening agents or other materials that would reduce the volatility of the iodine gas from the solution.

In addition to actual and prophetic working examples, fundamental research on the present technology has shown significant and real effects on the control of fungi, especially in residential or hospital environments. In particular, this technology can be compounded to fight *clostridium difficile* (c. diff.) spores in a healthcare setting. Since Syngenta has expressed interest in medical products, and you are currently designing experiments to yield efficacy data on spores, I request that you consider c. diff. under our investigational agreements. The inventor has raw data that we can get at least 4.5 log 10 reduction of strains of c. diff. including 20% spores, in water at pH 7.0. This work and protocol was designed by our GLP lab in Eagan, Minn. This result is enhanced by the activation of the reagents described above to produce the free iodine in an alcohol environment and/or also including iodate salts or periodate salts along with the iodide salts. These additional salts may be preferably present as from 0.05% by weight of the iodide salt to 50% by weight of the iodide salt (which is in approximately stoichiometric concentration with the other reagent, e.g., the cupric sulfate).

There is favorability in this technology as both reagents have alcohol solubility, so that we can produce free iodine in alcohol solutions, and thereby achieve very high (sterilizing) levels of disinfection in combination, well beyond what would be expected from estimating the individual effects. Healthcare is struggling to control c. diff. spores with acidified hypochlorite (free chlorine) solutions being among the most effective. However, this is dangerous for those having to clean and disinfect (housekeeping). The combined modes of action of ethanol or IPA and free iodine will manage c. diff. spread. The amount of water we choose to include in the alcohol would be largely determined by the contact times required to achieve high kill rates, with water slowing-down evaporation The above descriptions and examples are intended to provide enablement for practice of a generic concept of technology, and any specific numbers, compositions or terms used in the specification, unless specifically used in the following claims, are not intended to limit the scope of the invention claimed.

What is claimed is:

1. A process for reducing the microbial content in a confined area having an environment selected from the group consisting of vehicle cabs, vehicle seating areas, dishwashers, refrigerators, freezers and liquid circulation systems comprising providing at least two particulate reagents that react in the presence of water to form $I_2$ in the confined area to provide a concentration in aqueous material in the environment of at least 5 parts per million $I_2$/water, at least one of the at least two particulate reagents having a coating thereon that prevents atmospheric moisture from causing more than 5% of the reagents to react with each other to form $I_2$ when exposed for twelve hours to atmospheric moisture while particles containing the at least two reagents are in contact with each other in the environment, adding water to the two particulate reagents while they are in the confined area, and allowing the formed iodine to reduce microbial content within the confined area and throughout the environment of the confined area.

2. A process according to claim 1 for reducing the microbial content in the confined area comprising providing the at least two reagents that react in the presence of water to form $I_2$ in the environment, providing water to open the coating on the at least one particle, thereby to provide a concentration in aqueous material in the environment of at least 5 parts per million $I_2$/water wherein the two articulate reagents comprise KI and $Cu_2SO_4$.

3. The process of claim 2 wherein two reactants are added to the confined area and the two reactants react in the presence of water in or on the environment to generate a concentration of at least 10 parts $I_2$ per million in the water.

4. The process of claim 3 wherein the two reactants are mixed with mass in the confined area and at least some of the water present is ambient water in the environment.

5. The process of claim 3 wherein the two reactants are provided to the confined area and the confined area is closed and at least some of the water present is applied to the two reactants at about the same time as the provision of the two reactants into the confined area.

6. The process of claim 3 wherein at least one of the two reactants has been coated with a water soluble or water-dispersible coating to prevent premature reaction with another reactant and the confined area is selected from the group consisting of dishwashers, refrigerators and freezers.

7. The process of claim 3 wherein the reaction to form the molecular iodine is represented by $CuSO_4+KI^- \rightarrow Cu+K_2SO_4+I_2$.

8. The process of claim 3 wherein the two reactants are carried in a superabsorbent polymer.

9. A process for reducing the microbial content in a confined area having and environment, the process providing gaseous iodine throughout the environment of the confined area, the confined area selected from the group consisting of vehicle cabs, vehicle seating areas, dishwashers, refrigerators, freezers, and liquid circulation systems comprising providing at least two reagents in particulate form that react in the presence of water to form $I_2$ into the confined area and providing water to provide a concentration in aqueous material in vapor or liquid within the confined area of at least 10 parts per million $I_2$/water, at least one particle in particulate form having a coating thereon that prevents atmospheric moisture from causing more than 5% of the reagents to react with each other to form $I_2$ when exposed for twelve hours to atmospheric moisture at 60% relative humidity at 80° F., at least an antimicrobial amount of gaseous iodine being released within and retained in the confined area throughout the environment of the confined area.

10. The process of claim 9 wherein at least 50% of total gaseous stoichiometric $I_2$ formed in the confined area remains in the confined area for at least 2 minutes.

11. The process of claim 9 wherein at least 75% of total gaseous stoichiometric $I_2$ formed in the confined area remains in the confined area for at least 3 minutes.

12. The process of claim 9 wherein at least one of the two reagents that react to form $I_2$ are provided into the confined area with a covering of a water-soluble or water-dispersible material.

13. The process of claim 10 wherein at least one of the two reagents that react to form $I_2$ are provided into the confined area with a coating of a water-soluble or water-dispersible material.

14. The process of claim 9 wherein the at least two reagents that react to form $I_2$ are provided into the confined area within a packet or covering comprising a water-soluble or water-dispersible material.

15. The process of claim 14 wherein additional active agents than the at least two reagents are provided within the packet or covering, and there are at least two separate compartments within the packet or covering containing different reagents or an additional active agent.

16. The process of claim 1 wherein the reagents further comprise at least one halogen-providing compound selected from the class consisting of iodates, chlorates, bromates, periodates, perchlorates and perbromates.

17. The process of claim 9 wherein the at least one of the two reagents with a covering has a covering comprising a layer of hydrophilic silica stand off particles to form a discontinuous layer.

18. The process of claim 11 wherein the at least one of the two reagents with a covering has a covering comprising a layer of hydrophilic silica stand off particles to form a discontinuous layer.

19. The process of claim 1 wherein the at least one of the two reagents with a covering has a covering comprising a layer of hydrophilic silica stand off particles to form a discontinuous layer.

20. The process of claim 3 wherein the two reactants are carried in a superabsorbent polymer in addition to said coating.

21. The process of claim 3 wherein the at least one of the two reagents with a coating has a coating comprising a layer of hydrophilic silica stand off particles to form a discontinuous layer that disperses in the presence of water.

22. The process of claim 6 wherein the two reactants are carried in a superabsorbent polymer.

* * * * *